(12) United States Patent
Sudou et al.

(10) Patent No.: US 10,130,251 B2
(45) Date of Patent: Nov. 20, 2018

(54) VISION TESTING DEVICE AND VISION TESTING PROGRAM

(71) Applicant: CREWT MEDICAL SYSTEMS, INC., Tokyo (JP)

(72) Inventors: Fumitaka Sudou, Akishima (JP); Shinji Kimura, Tokyo (JP); Kenzo Yamanaka, Tokyo (JP); Tsuyoshi Onaka, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 0 days.

(21) Appl. No.: 15/307,904

(22) PCT Filed: Apr. 30, 2014

(86) PCT No.: PCT/JP2014/061934
§ 371 (c)(1),
(2) Date: Oct. 31, 2016

(87) PCT Pub. No.: WO2015/166548
PCT Pub. Date: Nov. 5, 2015

(65) Prior Publication Data
US 2017/0065166 A1    Mar. 9, 2017

(51) Int. Cl.
*A61B 3/10*      (2006.01)
*A61B 3/024*     (2006.01)
*A61B 3/08*      (2006.01)
*A61B 3/00*      (2006.01)
*A61B 3/032*     (2006.01)

(52) U.S. Cl.
CPC ............ *A61B 3/024* (2013.01); *A61B 3/005* (2013.01); *A61B 3/032* (2013.01); *A61B 3/08* (2013.01)

(58) Field of Classification Search
CPC ............ A61B 3/024; A61B 3/005; A61B 3/08
USPC ........ 351/200, 203, 205, 219, 222, 206, 246
See application file for complete search history.

(56) References Cited

U.S. PATENT DOCUMENTS 3,891,311 A * 6/1975 Fletcher ............... A61B 3/0083
                                                  351/200
5,223,865 A * 6/1993 Shirao ...................... A61B 3/02
                                                  351/239
(Continued)

FOREIGN PATENT DOCUMENTS

CN    201790795 U    4/2011
JP    H05-245105 A    9/1993
(Continued)

OTHER PUBLICATIONS

Jun. 17, 2014 International Search Report issued in International Patent Application No. PCT/JP2014/061934.
(Continued)

*Primary Examiner* — James Greece
(74) *Attorney, Agent, or Firm* — Oliff PLC

(57) ABSTRACT

A vision testing device and a vision testing program are capable of obtaining a correct test result while reducing an accumulation of fatigue added on one of the eyes of a testee, including: image displays that present a light for suppressing a dark adaptation for both eyes of a testee; and image displays that present a target for an eye (L, R, or both) of the testee so that the target is presented for one of the eyes before the vision testing for the other eye is ended.

16 Claims, 10 Drawing Sheets

(56) References Cited

U.S. PATENT DOCUMENTS

| | | | |
|---|---|---|---|
| 8,684,946 B1* | 4/2014 | Sims | A61B 3/032 |
| | | | 351/246 |
| 8,795,191 B2* | 8/2014 | Edwards | A61B 3/022 |
| | | | 351/246 |
| 2003/0002014 A1* | 1/2003 | Grant | A61B 3/10 |
| | | | 351/221 |
| 2007/0121071 A1* | 5/2007 | Jackson | A61B 3/0033 |
| | | | 351/246 |
| 2012/0127430 A1* | 5/2012 | Rotenstreich | A61B 3/024 |
| | | | 351/210 |
| 2012/0249951 A1 | 10/2012 | Hirayama | |
| 2013/0176534 A1 | 7/2013 | Frankfort et al. | |
| 2015/0150443 A1* | 6/2015 | Frankfort | A61B 3/113 |
| | | | 351/209 |
| 2015/0223682 A1* | 8/2015 | Kamkar | A61B 3/112 |
| | | | 351/206 |

FOREIGN PATENT DOCUMENTS

| | | |
|---|---|---|
| JP | H08-140933 A | 6/1996 |
| JP | H09-47430 A | 2/1997 |
| JP | 2012-213633 A | 11/2012 |
| JP | 2013-063318 A | 4/2013 |
| WO | 2008/100613 A2 | 8/2008 |

OTHER PUBLICATIONS

Nov. 3, 2017 Extended European Search Report issued in European Patent Application No. 14890769.4.

* cited by examiner

VISION TESTING DEVICE AND VISION TESTING PROGRAM

TECHNICAL FIELD

The present invention relates to a vision testing device and a vision testing program.

DESCRIPTION OF RELATED ART

It is difficult to obtain a Patient's own realization regarding an abnormality of a visual field. Therefore, there is a vision testing instrument typified by a vision testing. Various types are known as the vision testing instrument.

For example, there is a Humphrey perimeter as a general perimeter. In the Humphrey perimeter, the visual field is tested by displaying a target on a dome-shaped screen to check whether or not a testee recognizes the target. Usually shielding by an eye patch, etc., is applied to an opposite eye to an eye under test.

Further, patent document 1 teaches as follows: when the opposite eye to the eye under test is in a dark state during a vision testing, the opposite eye adapts to darkness progressively (called dark adaptation hereafter), thus requiring a time for the opposite eye to get used to brightness (called light adaptation hereafter), and having an influence on a test result.

Further, as the vision testing instrument, the instrument using a head mounted display (abbreviated as "HMD" hereafter) is known as a frame attachable to a head of the testee (for example, patent document 2).

PRIOR ART DOCUMENT

Patent Document

Patent document 1: Japanese Patent Laid Open Publication No. 1997-47430
Patent document 2: Japanese Patent Laid Open Publication No. 1996-140933

SUMMARY OF THE INVENTION

Problem to be Solved by the Invention

In the vision testing using a conventional vision testing instrument, after the vision testing for one of both eyes is ended, the vision testing is performed to the other eye. Therefore, in the Humphrey perimeter, shielding by patch, etc., is applied to the opposite eye to the eye under test. Accordingly, there is a problem that dark adaptation occurs while shielding the eye, and therefore in order to solve such a problem, a technique of patent document 1 is produced.

However, in the technique of performing the vision testing to one of the both eyes after end of the vision testing for the other eye, the following problem is involved.

One of the problems is that a learning effect occurs to the testee. The learning effect is that as a result of performing the vision testing by a left eye of the testee, the testee learns a pattern in which a target is displayed or a timing at which the target appears, and when the vision testing is performed by a right eye, a satisfactory result, namely, a result not reflecting an actual condition of the testee, is generated.

Another problem is that fatigue is accumulated in one eye. Usually, time required for the vision testing is about 4 minutes per one eye. The testee must continue to watch the target for 4 minutes by one eye, and thereafter must continue to watch the target for 4 minutes by the other eye. For example, when the vision testing is performed to the testee from the left eye first, there is a possibility that lack of concentration occurs when the right eye is tested thereafter, even if the concentration is maintained during test of the left eye. In such a case, there is a possibility that a correct result cannot be obtained in the vision testing of the right eye.

Therefore, a main object of the present invention is to provide a vision testing device and a vision testing program capable of obtaining a correct test result while reducing an accumulation of fatigue added on one of the eyes of the testee.

Means for Solving the Problem

As a strenuous effort by inventors of the present invention to solve the above-described problems, it is considered that the dark adaptation described in patent document 1 should also be solved. A background light is naturally presented together with a target for an eye under vision testing. Then, the inventors of the present invention achieve a technique of presenting a light for suppressing the dark adaptation, for the other eye not under the vision testing.

In addition, in order to solve the above-described problem, it is found by the inventors of the present invention to utilize a situation in which the light is presented for both eyes as a result. As a result, it is considered that from another point of view, the situation in which the light is presented for both eyes, is the situation in which both eyes shows the light adaptation and the both eyes prepare for the vision testing, and utilizing such a situation, a breakthrough knowledge is obtained such that test is not performed to one eye only, and the target is presented to the other eye before the vision testing for one eye is ended.

An aspect of the present invention based on the above-mentioned knowledge is as follows.

According to an aspect of the present invention, there is provided a vision testing device, including:
a dark adaptation suppressing light presenting unit that presents a light for suppressing a dark adaptation for both eyes of a testee; and
a target presenting unit that presents a target to one of the eyes of the testee so that the target is also presented to the other eye before a vision testing for the one eye is ended.

Advantage of the Invention

According to the present invention, a correct test result can be obtained while reducing an accumulation of fatigue added ib one of the eyes of a testee.

Figure 1:
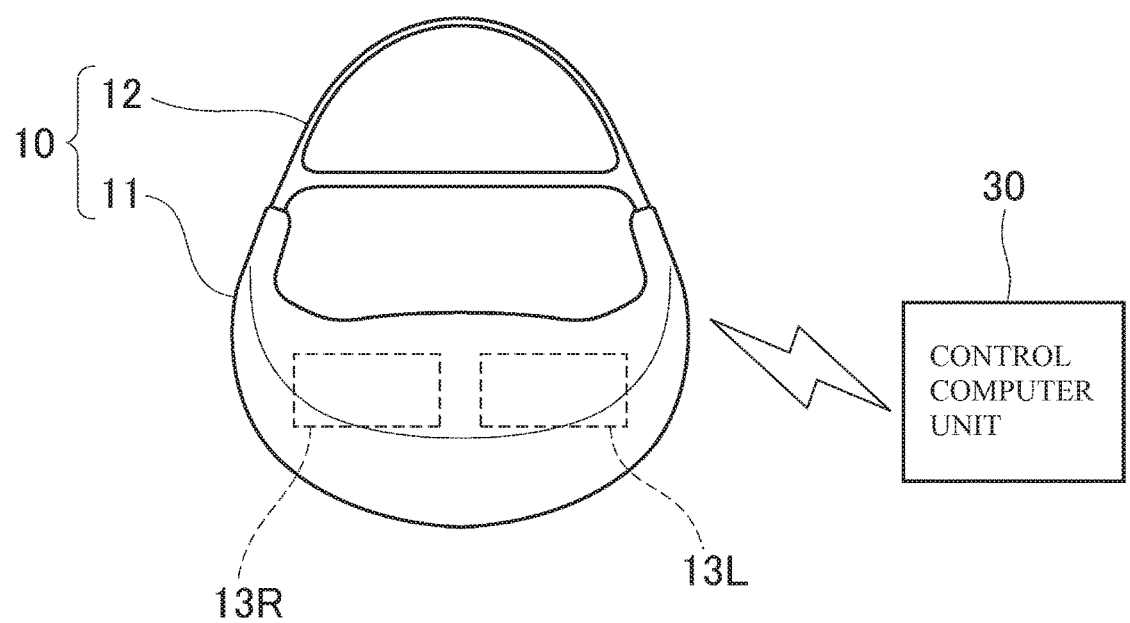
FIG. 1 is a schematic view of a vision testing device according to an embodiment.

Embodiments of the present invention will be described hereafter, with reference to the drawings. In the embodiments, explanation will be given in the following order.
1. Vision testing device
   A) HMD unit
      a. Image display (dark adaptation suppressing light presenting unit & target presenting unit)
      b. Others (optical system, etc.)
   B) Control computer unit
2. Relation between HMD unit and the control computer unit
3. Using method of the vision testing device
4. Vision testing program and recording medium
5. Effect of the embodiment
6. Modified example, etc.

A publicly-known vision testing device may be used for a configuration not described below. For example, configurations disclosed in patent document 1 (JPA1997-47430 and JPA1995-67833) may be used as needed.

1. Vision Testing Device

In this embodiment, explanation is given for a case in which the vision testing device is HMD.

FIG. 1 is a schematic view of a vision testing device. The vision testing device of this embodiment is roughly includes a head mount display (HMD) unit 10 and a control computer unit 30. The HMD unit 10 has a dark adaptation suppressing light presenting unit and a target presenting unit. However, this embodiment shows a case in which the dark adaptation suppressing light presenting unit and the target presenting unit are collected in an image display 13.

In the explanation hereafter, a left eye is expressed by L, and a right eye is expressed by R. However, marks such as L and R is omitted when explanation is given for "each eye", "right and left eye (both eyes)", or a configuration like "a configuration for a left eye". L is added to the end of signs and numerals of the configuration for the left eye, and R is added to the end of signs and numerals of the configuration for the right eye. Signs and numerals not added with L or R, indicate the configurations that are not used specifically for each eye, or indicate collectively the configuration for the left eye and the configuration for the right eye.

A) HMD Unit 10

HMD unit 10 includes a housing 11 and a wearing band 12 connected thereto, so that a person subjected to a vision testing (simply referred to a "testee" hereafter) can wear the HMD unit 10 on his/her head. Further, a dark adaptation suppressing light presenting unit and a target presenting unit are assembled in the housing 11. This embodiment shows a case in which image displays (13L and 13R) provided for the right and left eyes respectively, have both of the dark adaptation suppressing light presenting unit and the target presenting unit. Sing and numeral (13L and 13R) are collectively expressed as "image display 13" hereafter, while 13L indicates the image display for the left eye, and 13R indicates the image display for the right eye.

a. Image Display 13 (Dark Adaptation Suppressing Light Presenting Unit & Target Presenting Unit)

Figure 2:
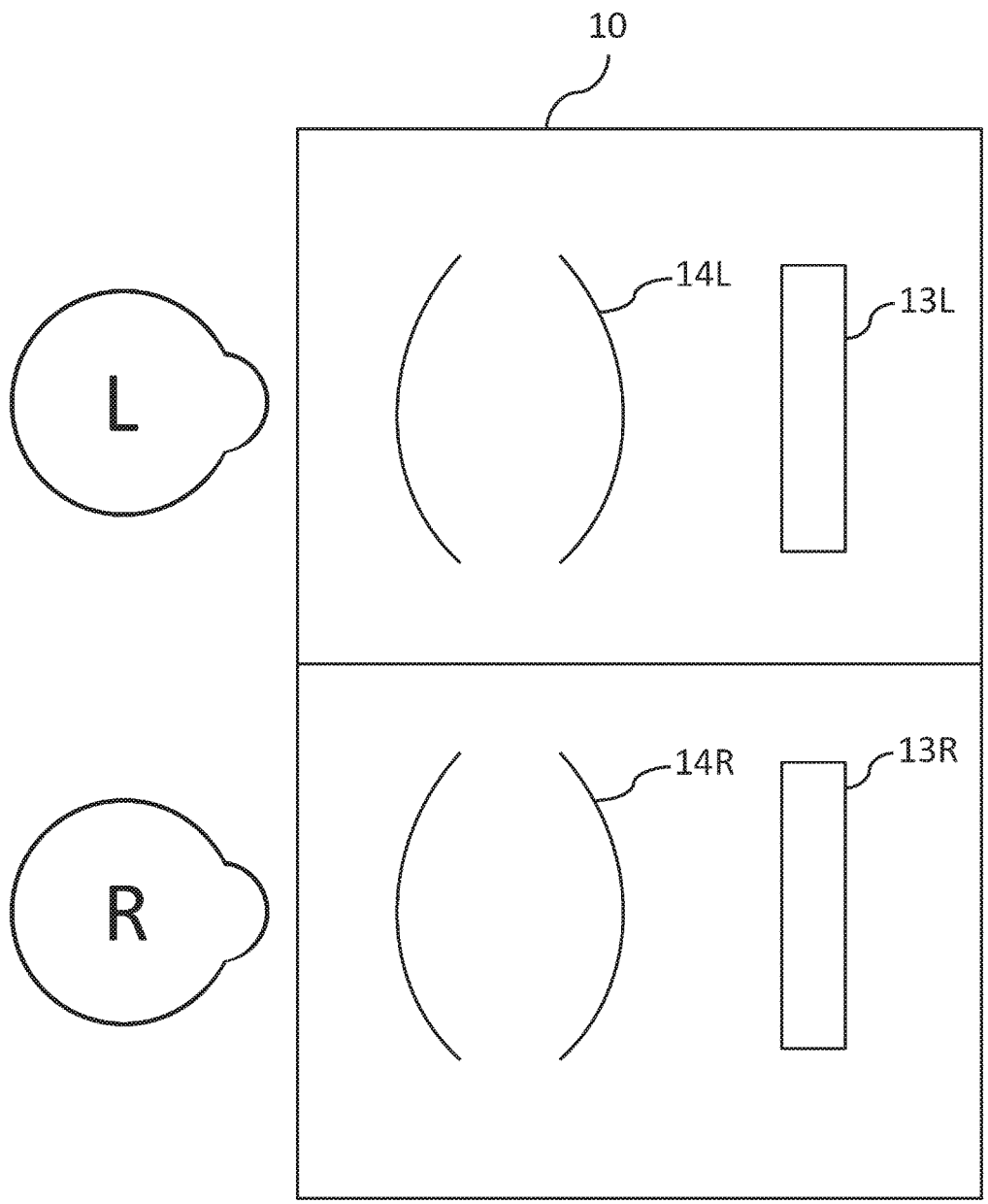
FIG. 2 is a top schematic view of the vision testing device according to an embodiment of the present invention.

The image display 13 is schematically illustrated in FIG. 2. FIG. 2 is a top schematic view of the vision testing device according to an embodiment.

The image display 13 is disposed in front of the eye of the testee who wears the HMD unit 10, to thereby perform image display for the testee. It is conceivable to use the image display 13 configured using LCD (Liquid Crystal Display) for example. The image of a background light and the target in combination, can be given as the image displayed and outputted by the mage display 13.

The "background light" presented by the dark adaptation suppressing light presenting unit is the light that controls brightness and color of a background of the target presented for the eye. In this embodiment, the "background light" is the "light for suppressing a dark adaptation". The target is displayed under presence of the background light. The background light may be presented by preparing a background image, or a prescribed light may be simply presented. Regarding the brightness of the background light, the brightness of not allowing the dark adaptation to occur in the right and left eyes, may be acceptable. Further, the background light may be presented intermittently to a degree not allowing the dark adaptation to occur (i.e. intermittent on/off of a light source of the background light, namely, open/close of a shutter), even if the background light is not continuously presented. Further, regarding the color of the background light, any color may be used depending on the type of the vision testing. However, from a viewpoint of improving a precision of the vision testing, a white light is preferable.

The image display 13 of this embodiment is configured to respond to a test image for the left eye and a test image for the right eye individually, that is, is configured by a display panel for the left eye and a display panel for the right eye. At this time, it is preferable to present the background light with the same brightness in each image display (13L and 13R) as described later. However, it is no problem in presenting the background light with a different brightness.

The "target" presented by the target presenting unit, is displayed for testing a vision. There is no particular limit in the target. For example, during glaucoma test, a point of light is displayed over the background light, and a location of the point of light (white circle used in FIG. 3) is varied and displayed, to thereby check presence/absence of a lost visual field and a location of the lost visual field, and create a visual field map collectively including such information. Further, Landolt ring as the target, Snellen target using alphabet, E-chart using E-shape only, or other Hiragana and Katakana may be used.

In addition, not only a static visual field measurement that displays a static point of light (target) over the background light, but also a dynamic visual field measurement that displays the target as a moving point of light, may be performed.

(Dark Adaptation Suppressing Light Presenting Unit)

As described above, in this embodiment, the image display (13L and 13R) has both of the dark adaptation suppressing light presenting unit and the target presenting unit. The dark adaptation suppressing light presenting unit of this embodiment is the unit for presenting a light (i.e. background light) for suppressing dark adaptation, and such a light is the light to be presented to the right and left eyes. In other words, when the vision testing is performed to one of the right and left eyes and the vision testing is not performed to the other eye of the right and left eyes of the testee, the dark adaptation suppressing light presenting unit presents the light to the other eye as well, for suppressing the dark adaptation.

More specifically, the dark adaptation suppressing light presenting unit is a light source mounted on each image display (13L and 13R). The dark adaptation suppressing light presenting unit may be the light source mounted on a portion other than the image display (13L and 13R), and of course may be the light source mounted on a portion other than the image display (13L and 13R). In other words, the dark adaptation suppressing light presenting unit and the target presenting unit may be configured as separate bodies. As other configuration pattern, a technique of irradiating the image display 13 with a light from other portion of the HMD unit 10 using the image display 13 as a screen, so that the light for suppressing the dark adaptation is presented to the eye of the testee.

In addition, a configuration as a part of the dark adaptation suppressing light presenting unit may be added to an optical system 14 as will be described later in (b. Others (optical system, etc.)), the configuration including a polarizing film, a polarizer, a polarizing beam splitter, and an active shutter, etc., which are described in <6. Modified example, etc.> described later.

The dark adaptation suppressing light presenting unit is the unit for presenting a light (i.e. background light) for suppressing a dark adaptation. Therefore, in the right and left eyes of the testee, the background light presented to one of the eyes not under the vision testing, may be presented with a low dose of irradiation to a minimum possible extent to suppress the dark adaptation, compared to the background light presented to the other eye under the vision testing, or the background light may be intermittently presented to one of the eyes while the background light is presented continuously to the other eye. On the other hand, vision testing conditions can almost be the same in the right and left eyes, if the condition of the presented background light (such as brightness) is the same in the right and left eyes. In such a case, when the vision testing is performed alternately to each of the right and left eyes by the target presenting unit, preferably a difference due to the vision testing condition is not likely to occur in the test result for the right and left eyes. The "brightness of the background light" called here, is the brightness sensed by human eyes, and can be expressed by luminance or irradiation dose.

(Target Presenting Unit)

The target presenting unit of this embodiment is a portion for presenting a target to the eye of the testee, in such a manner that the target is presented to one of the eyes of the testee before the vision testing for the other eye is ended.

In the specification of the present invention, when all tests for one of the eyes are ended, this state is called an "end of the vision testing". If the target is scheduled to be presented five times for the right eye, the "end of the vision testing" means that all of the five times of the presentation of the target are ended. On the other hand, the step of performing the presentation of the target of each time (for example, the step from presentation of the first target to a disappearance of the target) is called "performing presentation of the target".

The "presentation of the target to the eye of the testee" includes a case in which the target is presented to right and left eyes at once although the vision testing is eventually performed to the right and left eyes, and also includes a case in which the target is presented to one of the right and left eyes when presenting one target. These cases are called "presentation of the target to at least one of the eyes". "Before end of the vision testing performed to one of the eyes" includes a case in which the target is presented to one of the eyes at the end of the vision testing for the other eye, and also includes a case in which the target is presented to other eye at the start of the vision testing. Therefore, the case in which the target is presented to right and left eyes at once, matches a definition that "the target is presented to one of the eye of the testee so that the target is presented to the other eye of the testee before the vision testing for the other eye is ended".

"Presentation of the target to at least one of the eyes" indicates a state in which the target is presented selectively to the right or left eye, and indicates a state in which the target is presented to both of the right and left eyes. In other words, when the target is presented, there is a state in which at least one of the right eye or the left eye can recognize the target. Further, the test result of the right eye and the test result of the left eye can be separately obtained by presenting the target to one of the right eye or the left eye. It is also useful to present the target to both of the right and left eyes. As such a case, a case of creating a visual field map in binocular vision can be considered, to examine the visual field at the time of driving vehicles. Further, the target may be presented by suitably combining the "presentation of the target to one of the right eye or the left eye" and "presentation of the target to both of the right and left eyes".

When the target is presented to one of the right eye or the left eye, the target may be alternately presented to the right and left eyes. "Alternately" called here is not used in the meaning that "the test is performed to only one of the eyes (right eye R), but used in the meaning that the tests is performed to the left eye L in such a manner as interrupting the test for the right eye R". "Alternately" in this specification includes a case in which the target indicating a plurality of points (or a single point) in the visual field map is presented to the left eye L after the target indicating a plurality of points in the visual field map is presented to the right eye R, and the target indicating a plurality of points (or a single point) in the visual field map is presented to the right eye R. Of course "alternately" in this specification also includes a case in which the number of times of presenting the target to each of the right and left eyes is set to a single time, in such manner that the target indicating one point in the visual field map is presented to the left eye L after the target indicating one point in the visual field map is presented to the right eye R, and again the target indicating one point in the visual field map is presented to the right eye R and again the target indicating one point in the visual field map is presented to the left eye L, and such a presentation of the target is repeatedly performed.

Figure 3:
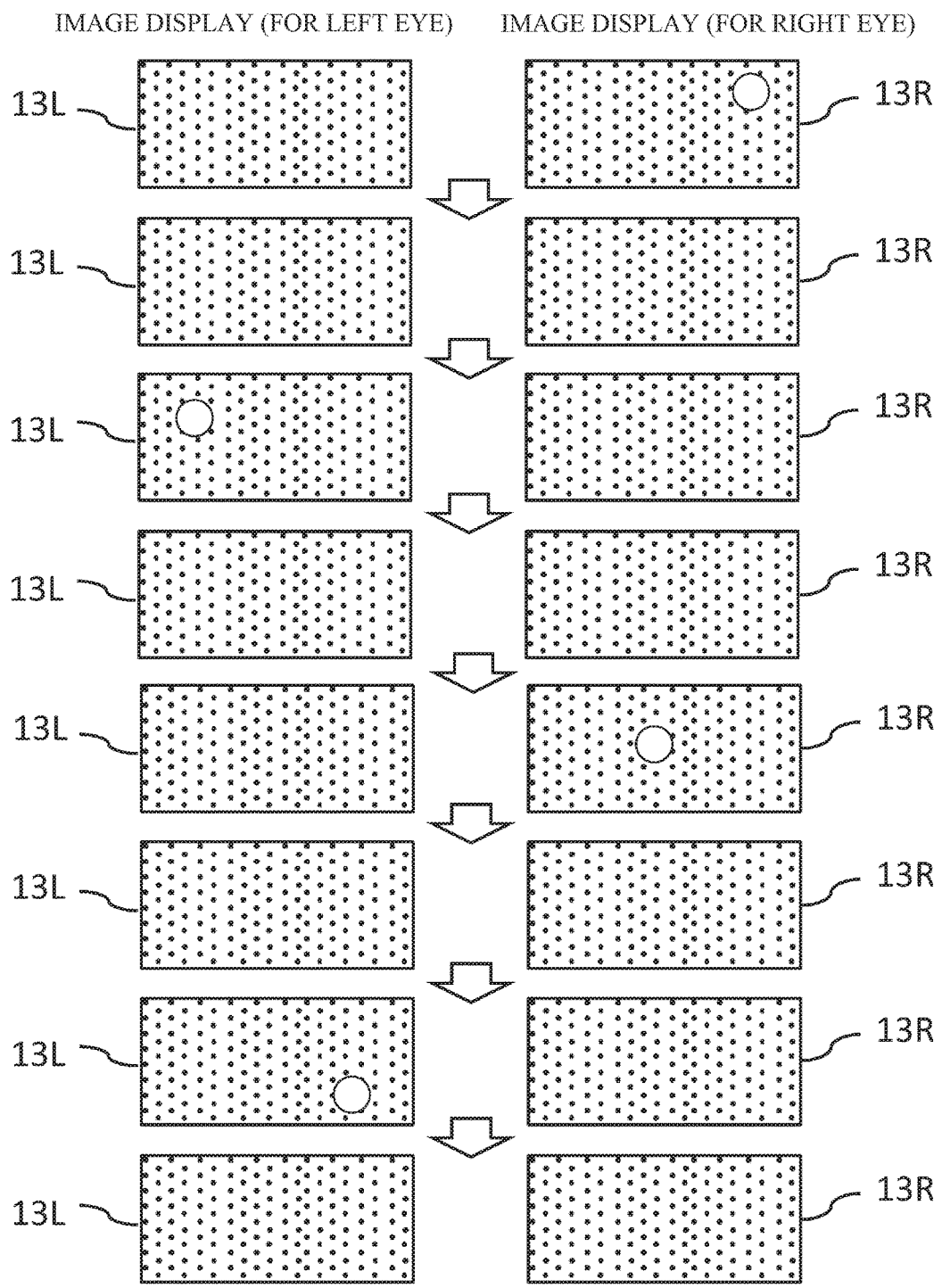
FIG. 3 is a view illustrating a using method of the vision testing device according to an embodiment of the present invention.

In any case, in this embodiment, the test is not performed to only one eye (right eye R), but performed to the left eye L in such manner as interrupting the test for the right eye R. FIG. 3 schematically illustrates such a state. FIG. 3 is a view illustrating a using method of the vision testing device of this embodiment. In FIG. 3, it appears that the number of times of presenting the target (white circle (o) in the figure) to each of the right and left eyes is set to a single time, but multiple number of times of presentation of the target is also acceptable at the time of the first test for the right eye R for example, although it is a matter of course the case of a single time is included.

Further in FIG. 3, an interval of one second is provided after presentation of one target, as is performed in a usual vision testing. At the time of the interval, the light for suppressing the dark adaptation is presented to both of the right and left eyes. The time required for the interval may be suitably set depending on a situation. Further, whether or not the interval is provided, may be suitably set, depending on a situation.

Regarding a technique of presenting the target, a publicly-known technique may be used. For example, the visual field map may be created by making a particular prescribed portion bright in the image display 13, and confirming whether or not the testee can recognize the light of this portion. Conversely, it is also acceptable to turn-off the light source of the prescribed portion of the image display 13, darken a prescribed portion particularly, and confirm whether or not the testee can confirm the dark portion. Of course, it is also acceptable to present the target having a prescribed shape as described above.

As a function of the target presenting unit, there is a function of performing the vision testing for one of the eyes before the vision testing is ended for the other eye. Owing to this function, "generation of a learning effect can be suppressed" and "accumulation of fatigue added on one of the eyes of the testee can be reduced" and "a correct test result can be obtained".

As an example, explanation is given hereafter regarding a case in which the vision testing for the left eye L is performed in a form of interrupting the test for the right eye R like right eye→left eye→right eye.

First, regarding the "suppression of generation of the learning effect", the test can be performed for the left eye L before the learning effect of the right eye R is reflected on the left eye L, because the test for the left eye L is performed before the test for the right eye R is ended. Similarly, during the rest of the test for the right eye R, the learning effect due to the test already performed for the right eye R can be weakened.

Regarding "reducing the accumulation of fatigue added on one of the eyes of the testee due to continuous test of the eye", it is possible to suppress an influence on the test result of the left eye L due to excessive concentration on the test for the right eye R, because the test for the left eye L is performed before the test for the right eye R is ended. Usually, when the test for the right eye R is performed, the left eye L tries to see the target following the right eye R. However, conventionally the left eye L is shielded by an eye patch, etc. As a result, the left eye L is in a continuous concentration state similarly to the right eye R, while being in a state of not viewing the target even if the left eye L tries to do so. When the test for the left eye L is actually performed, the test for the left eye L is continuously performed with almost no rest, although the left eye L also concentrates on the test during the test for the right eye R for four minutes. Therefore, the test result of the left eye L is not made based on a normal state.

On the other hand, the test is started for one of the eyes (in other words, the target is presented) before a series of the test for the other eye is ended. As a result, it is unnecessary to perform the test in a bias state of fatigue toward one of the eyes. In other words, the testee can receive the test while holding the same degree of concentration in the right and left eyes.

This embodiment utilizes a situation in which the light is presented to the right and left eyes to suppress the dark adaptation, and in this state, employs a configuration in which the above-described function can be achieved.

The above-described function is further increased when the presented brightness of the background light is the same in the right and left eyes. In other words, when the vision testing condition is made to be the same as much as possible in the right and left eyes by presenting the same brightness of the background light for the right and left eyes, it is almost impossible to judge whether the target is presented to the right eye R, or whether the target is presented to the left eye L, even if the target is presented to the testee. On the other hand, for which of the right and left eyes the target is presented, can be grasped by an operator of the device, and a result thereof can also be grasped. Therefore, there is no necessity for having a preconception by the testee as follows: "the test is performed now for an uncomfortable eye", and the testee is not required to prepare for the rest of the test as follows: "the test for the left eye is still left even if the test for the right eye is ended". By performing the test (once in total) collectively for the right and left eyes, rather than performing the test for each eye one by one (once for the left eye+once for the right eye=twice in total) (actually even in a case of the test for each eye one by one), the fatigue is not accumulated on each eye, and mental fatigue of the testee is reduced.

b. Others (Optical System, Etc.)

In the HMD unit 10, an optical system 14 may be provided between the image display 13 and the eye of the testee, so that the testee can confirm the target. Further, as illustrated in FIG. 2, an optical system 14L for the left eye and an optical system 14R for the right eye may be separately provided. The optical system 14 may have a configuration described in the abovementioned patent documents, or the optical system 14 of a publicly-known vision testing may be used. As such an optical system 14, a combination of optical elements such as an eyepiece lens, an objective lens, and mirrors, etc., can be given.

As the configuration of the optical system 14, although not illustrated, a sensor for adjusting a luminous intensity, a glare generator, a glare backlight generator, and an exciter for displaying the target on the image display 13, can be given. Further, a signal generator for displaying an intention of the testee such that he/she confirms the target, a memory for storing the signal, and a test monitor for displaying the result, or the like can be given.

B) Control Computer Unit 30

The control computer unit 30 has a function as a computer device that performs information processing indicated based on a prescribed program, and specifically is configured by a combination of CPU (Central Processing Unit), HDD (Hard disk drive), ROM (Read Only Memory), RAM (Random Access Memory), and External Interface (I/F), etc. The control computer unit 30 may be assembled in the housing 11 of the HMD unit 10, or may be provided separately from the HMD unit 10. When the control computer unit 30 is provided separately from the HMD unit 10, communication between the control computer unit 30 and the HMD unit 10 can be carried out via wire or wireless communication line.

2. Relation Between the HMD Unit 10 and the Control Computer Unit 30

A relation between the control computer unit 30 and the HMD unit 10 according to this embodiment will be described hereafter.

Figure 4:
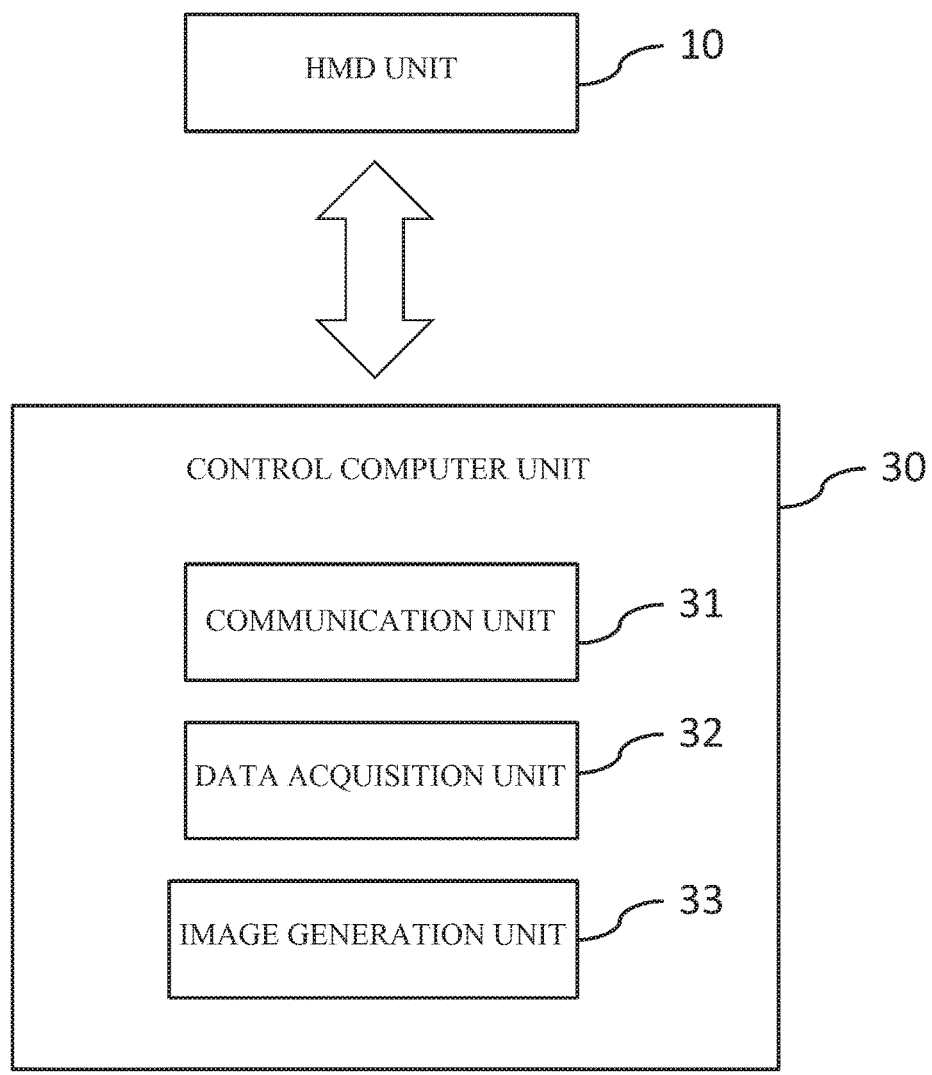
FIG. 4 is a block diagram illustrating a relation between a control computer section and HMD section according to an embodiment of the present invention.

FIG. 4 is a block diagram illustrating the relation between the control computer unit 30 and the HMD unit 10.

In a simulation device of this embodiment, the functions as a communication unit 31, a data acquisition unit 32, and an image generation unit 33 are realized, by executing a prescribed program (vision testing program described later) by the control computer unit 30.

The communication unit 31 has a function of carrying out communication between the control computer unit 30 and the HMD unit 10. Specifically, the communication unit 31 transmits a simulation image generated by the image generation unit 33 described later, to the image display 13. A communication protocol used by the communication unit 31 is not particularly limited.

The data acquisition unit 32 has a function of acquiring information regarding the testee. The acquired information may include physiological data of the testee such as age and gender. Such physiological data may be acquired, for example by accessing a data server device on a network line by the data acquisition unit 32 of the control computer unit 30, via the network line not illustrated. Then, the test condition information such as brightness and color of the background light, the type of the target and the time for presenting the target, and the timing for alternately presenting the target for the right and left eyes, may be automatically set in association with the physiological data acquired by the data acquisition unit 32. Of course, an operator who performs the test may input the physiological data manually, and in this case, the data acquisition unit 32 is not required.

The image generation unit 33 has a function of presenting an image obtained by superposing the background light and the target, which is the image viewed by the testee with the left eye L and the right eye R. A test image is generated based on the physiological data and the test condition information acquired by the data acquisition unit 32, or the physiological data and the test condition information inputted manually. Then, the generated image is displayed on the image display 13.

The communication unit 31, the data acquisition unit 32, and the image generation unit 33 described above, are realized by executing a vision testing program (described later) of this embodiment by the control computer unit 30 having a function as a computer device. In this case, the vision testing program is used by being installed on the HDD, etc., of the control computer unit 30, but prior to the installment, it may be provided via the network line connected to the control computer unit 30, or may be provided by being stored in a computer readable recording medium that can be read by the control computer unit 30.

3. Using Method of the Vision Testing Device

A using method of a vision testing device of this embodiment will be described next.

Figure 5:
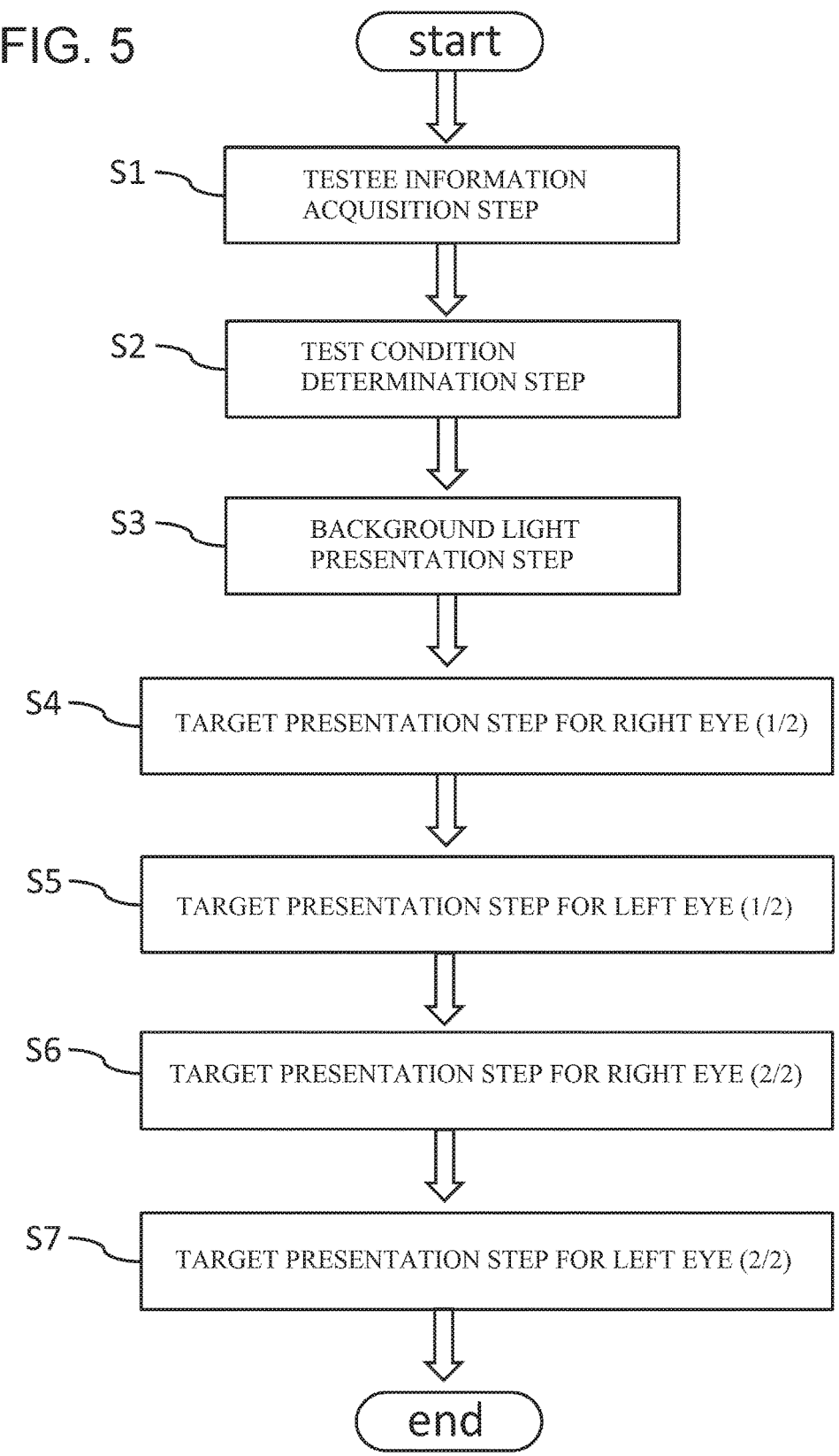
FIG. 5 is a flowchart illustrating the using method of the vision testing device according to an embodiment of the present invention.

FIG. 5 is a flowchart illustrating the using method of the vision testing device of this embodiment.

The using method of the vision testing device described in this embodiment will be described below. A case of staring the test from the right eye R will be described hereafter, and explanation is also given for a case (the abovementioned case of FIG. 3) of performing two sets of the test like right eye→left eye→right eye→left eye (right eye→left eye). Although not illustrated in FIG. 5, several seconds of interval may be provided for presenting only the background light without presenting the target for both of the right and left eyes as illustrated in FIG. 3.

The using method of the vision testing device is roughly includes a testee information acquisition step (S1), a test condition determination step (S2), a background light presentation step (S3), a target presentation step (1/2) (S4) for the right eye R, a target presentation step (1/2) (S5) for the left eye L, a target presentation step (2/2) (S6) for the right eye R, and a target presentation step (2/2) (S7) for the left eye L.

In the testee information acquisition step (S1), information regarding the testee is acquired by the data acquisition unit 32. For example, by inputting the identification number of the testee by the operator of the device, inquiry of the information regarding the testee is performed to the data server device via the communication unit 31. Then, the physiological data of the testee stored in the data server device is transmitted to the data acquisition unit 32 via the communication unit 31. Of course, the vision testing device may acquire the testee information by inputting the testee information manually by the operator.

In the test condition determination step (S2), the test condition information such as brightness and color of the background light, the type of the target and the time for presenting the target, and the timing for alternately presenting the target for the right and left eyes, may be automatically set in association with the physiological data acquired by the data acquisition unit 32. Of course, the test condition may be arbitrarily determined manually by the operator.

In the background light presentation step (S3), the brightness and the color of the light source of the image display 13 are determined based on the test condition information determined by the test condition determination step (S2). At this time, the same background light is presented to not only the image display 13L corresponding to one of the eyes (for example, the left eye L), but also the image display R corresponding to the other eye (the right eye R), thus creating a situation in which the dark adaptation does not occur in both of the right and left eyes.

In the target presentation step (1/2) (S4) for the right eye R, first, the vision testing is performed for the right eye R. The timing for alternately presenting the target for the right and left eyes, is set based on the test condition information determined in the test condition determination step (S2). As a result, the test image is generated in the background light presentation step and the target presentation step.

Then, after the target presentation step (1/2) (S4) for the right eye R is ended, the target presentation step (1/2) (S5) for the left eye L is performed. That is, only half of the test for the right eye R is ended at this time point. The test for the left eye L is performed after the test for the right eye R is suspended.

In the target presentation step (1/2) (S5) for the left eye L, the test similar to the test for the right eye R is performed. After the target presentation step (1/2) (S5) for the left eye L is ended, the target presentation step (2/2) (S6) for the right eye R is performed. In other words, this time, the test for the left eye L is suspended, and thereafter the test for the right eye R which has been suspended earlier is restarted.

The target presentation step (2/2) (S6) for the right eye R, and the target presentation step (2/2) (S7) for the left eye L are performed similarly to (S4) and (S5). Thus, the vision testing for the right and left eyes is completed.

4. Vision Testing Program and Recording Medium

In this embodiment, there is a great characteristic in the vision testing device having the abovementioned configuration. On the other hand, there is also a great characteristic in the program and the recording medium capable of causing the computer device to function as the "dark adaptation suppressing light presenting unit" and the "target presenting unit". In this case, as a specific operation method, the control compute unit 30 gives an instruction to the dark adaptation suppressing light presenting unit to present a prescribed light. Similarly, the control computer unit 30 gives an instruction to the target presenting unit to present the target under a prescribed condition. The content of the instruction may be determined based on the information regarding the testee acquired by the data acquisition unit 32. Similarly, based on the information, the content of the instruction is reflected on the image generation unit 33, and the image may be displayed on the image display 13.

Of course, setting of the condition of the dark adaptation suppressing light presenting unit and the target presenting unit can be performed manually by the operator of the device. However, by using the vision testing program of this embodiment, presentation of the dark adaptation suppressing light and presentation of the target can be automatically performed under a proper condition in accordance with the testee.

5. Effect of the Embodiment

In this embodiment, the background light is presented naturally to the eye under the vision testing. Then, even if there is the other eye not under the vision testing, the light for suppressing the dark adaptation is presented to the other eye. As a result, first, reduction in the precision of the test result due to the dark adaptation can be suppressed.

Then, in this embodiment, the target is presented to the eye of the testee, so that the target is presented to one of the eyes before the vision testing for the other eye is ended, utilizing a situation in which the light for suppressing the dark adaptation is presented, that is, a situation in which the right and left eyes are in a state of light adaptation, to thereby prepare the vision testing for the right and left eyes. Thus, "generation of the leaning effect is suppressed", and "accumulation of fatigue added on one of the eyes of the testee due to continuous test of the eye is reduced" are achieved.

As a result, according to this embodiment, a correct test result can be obtained while reducing the accumulation of fatigue added on one of the eyes of the testee.

6. Modified Example, Etc.

The present invention is not limited to the above-described content of the embodiments, and can be suitably modified in a range not departing from the gist of the invention.

Other example of the dark adaptation suppressing light presenting unit will be described hereafter. By providing a configuration as a part of the dark adaptation suppressing light presenting unit in the optical system 14, the light for suppressing the dark adaptation may be presented to the eye not under the vision testing.

Other example of the dark adaptation suppressing light presenting unit will be described hereafter.

[Example of Using a Polarizing Film 13α and a Polarizer 15]

Figure 6:
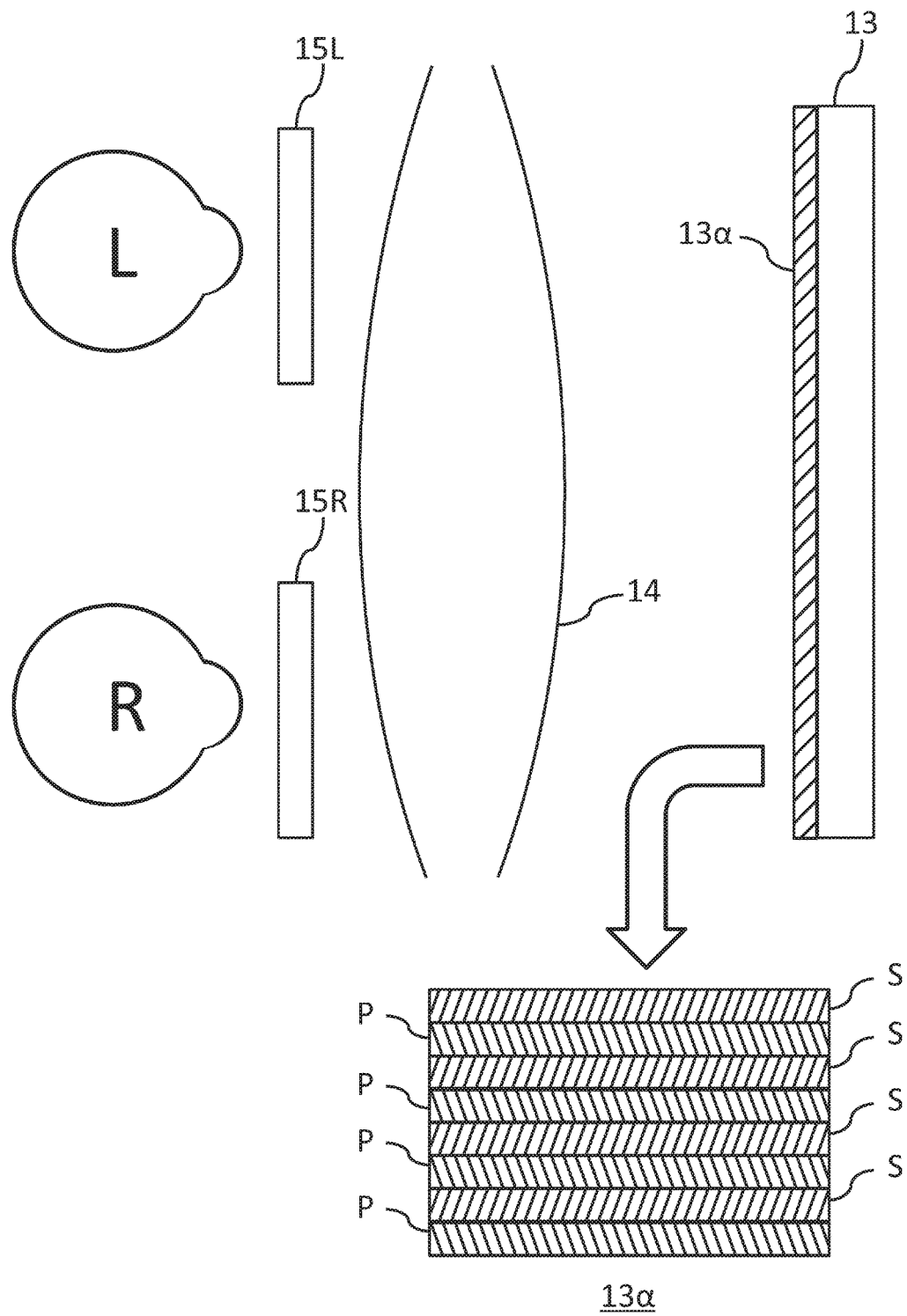
FIG. 6 is a top schematic view of a vision testing device using a polarizer and a polarizing film, according to another embodiment, wherein an arrow head indicates a front schematic view of the polarizing film.

First, explanation will be given hereafter using FIG. 6. FIG. 6 is a top schematic view of the vision testing device according to another embodiment, in which a polarizing film 13α and a polarizer 15 are used, wherein an arrow head indicates a front schematic view of the polarizing film.

As illustrated in FIG. 6, one image display 13 is prepared unlike the abovementioned embodiment. Then, the polarizing film 13α is stuck to the image display 13. The polarizing film 13α has two types of polarizing pattern (P polarizing pattern (P) and S polarizing pattern (S)). Then, a polarizer 15L for P-polarization is arranged between the left eye L and the optical system 14, and a polarizer 15R for S-polarization is arranged between the right eye R and the optical system 14. Thus, the background light of P-polarization is presented to the left eye L, and the background light of S-polarization is presented to the right eye R, regarding the background light emitted from one image display 13. Therefore, even if the vision testing is performed to one of the eyes, the dark adaptation does not occur in the other eye.

The target is presented in the following manner. When the target is presented to the left eye L, the target is presented to a portion having the P polarizing pattern in the polarizing film 13α on the image display 13. Similarly, when the target is presented to the right eye R, the target is presented to a portion having the S polarizing pattern. The polarizer 15L for P-polarization may be arranged, or the polarizer 15L for S-polarization may be arranged between the left eye L and the optical system 14. The same is applied to the right eye R.

In the modified example described here, the dark adaptation suppressing light presenting unit includes the image display 13. Further, the target presenting unit includes the image display 13 to which the polarizing film 13α is stuck, and polarization.

[Example of Using the Polarizer 15 and a Polarization Beam Splitter 16]

Figure 7:
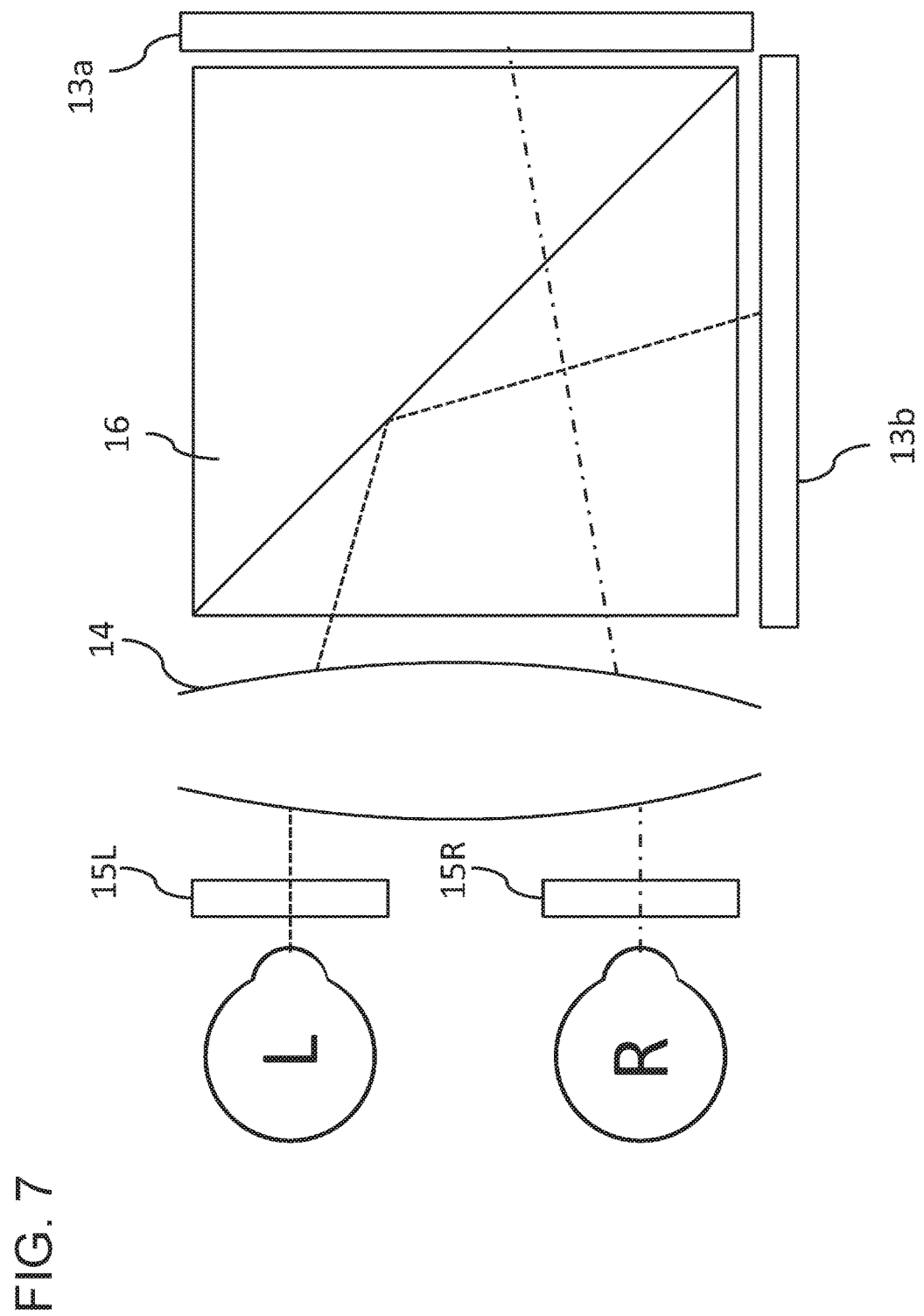
FIG. 7 is a front schematic view of a vision testing device using a polarizer and a polarizing beam splitter, according to another embodiment of the present invention.

Explanation will be given next using FIG. 7. FIG. 7 is a front schematic view of a vision testing device using a polarizer 15 and a polarizing beam splitter, according to another embodiment of the present invention.

As illustrated in FIG. 7, unlike the abovementioned embodiment, one image display 13a is prepared in front of the right and left eyes, and an image display 13b is prepared separately from the image display 13a, so that the image displayed on the image display 13a is set in a mirror image relation, and the polarizing beam splitter 16 is arranged between the optical system 14 and the image display (13a and 13b). Then, the polarizer 15L for P-polarization is arranged between the left eye L and the optical system 14, and the polarizer 15R for S-polarization is arranged between the right eye R and the optical system 14. Thus, for example, the background light and the target of the separately prepared image display 13b are presented to the left eye L by the polarizer 15L for P-polarization and the polarizing beam splitter 16. On the other hand, the background light and the target of the image display 13a in front of the right and left eyes are presented to the right eye R by the polarizer 15R for S-polarization and the polarizing beam splitter 16.

In the modified example described here, the dark adaptation suppressing light presenting unit and the target presenting unit include two image displays (13a and 13b) and the polarizing beam splitter 16.

[Example of Using the Polarizer (15 and 21) and a Polarization Holding Screen 17]

Figure 8:
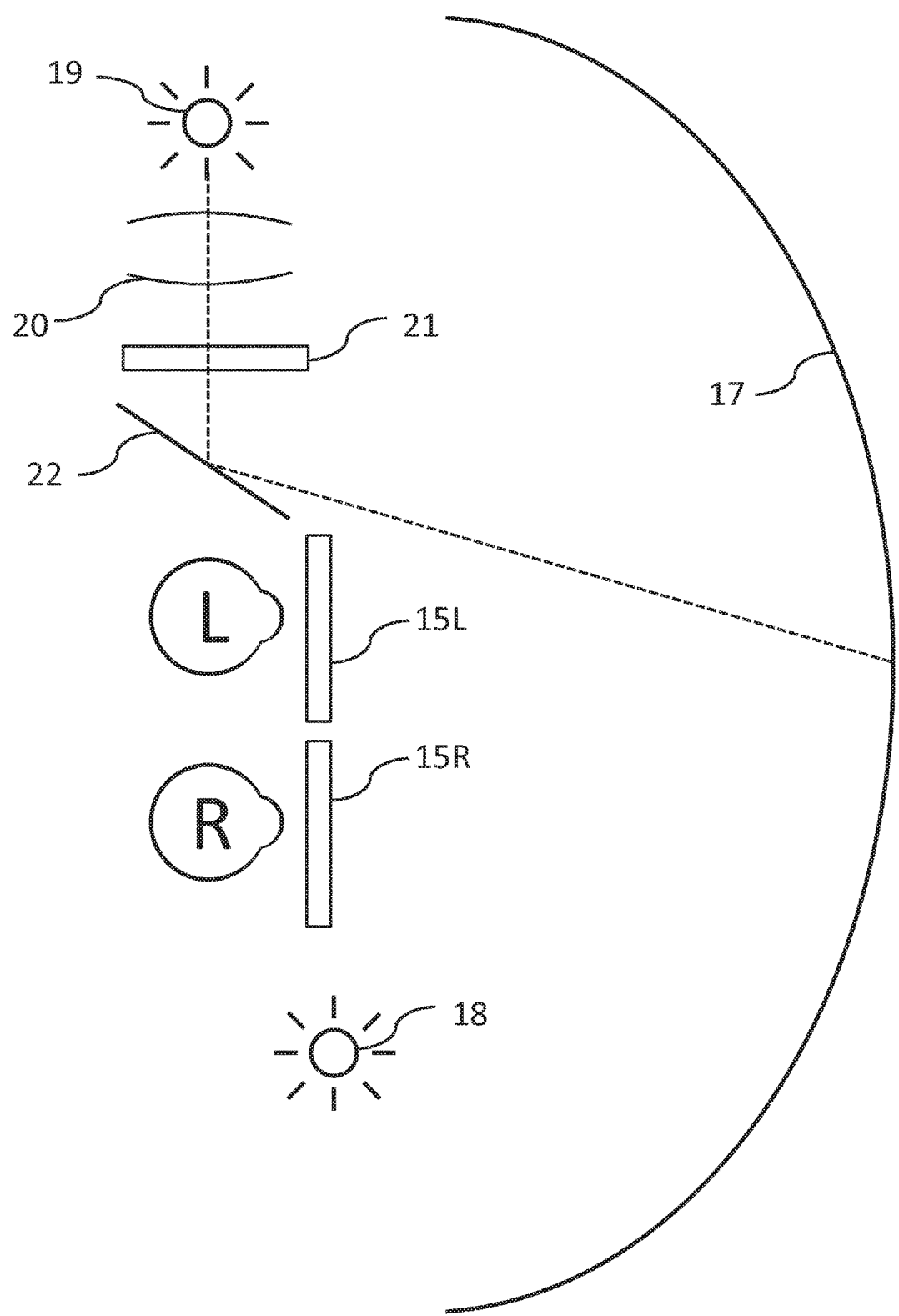
FIG. 8 is a front schematic view of a vision testing device using a polarizer and a screen, according to another embodiment.

Explanation will be given next, using FIG. 8. FIG. 8 is a front schematic view of a vision testing device using a polarizer and a polarization holding screen 17, according to another embodiment.

As illustrated in FIG. 8, unlike the abovementioned embodiment, a light source 18 of a non-polarized light is prepared in the dark adaptation suppressing light presenting unit in a state of preparing one dome type polarization holding screen 17 in front of the right and left eyes, to thereby present the background light to both of the right and left eyes. Then, the target presenting unit is configured to arrange the polarizer 15L for P-polarization between the left eye L and the polarization holding screen 17, and the polarizer 15R for S-polarization between the right eye R and the polarization holding screen 17, irradiate the polarization holding screen 17 with a light emitted from the light source 19 prepared separately from the dark adaptation suppressing light presenting unit and passing through the optical system 20 and the polarizer 21 for the target, and reflected by a reflector 22. By varying an angle of the reflector 22, the target can be presented to the portion of the screen corresponding to a prescribed place in the visual field map. Even if the image display 13 is not provided for each of the right and left eyes, and with a configuration employing the screen common in the right and left eyes, the dark adaptation suppressing light presenting unit and the target presenting unit can exhibit the function thereof.

In the modified example described here, the dark adaptation suppressing light presenting unit includes the light source 18 of non-polarization. Further, the target presenting unit includes the light source, the polarizer 21, and the polarization holding screen 17 prepared separately from the dark adaptation suppressing light presenting unit.

[Example of Using an Active Shutter 23 and a Time Division Display Device 24]

Figure 9:
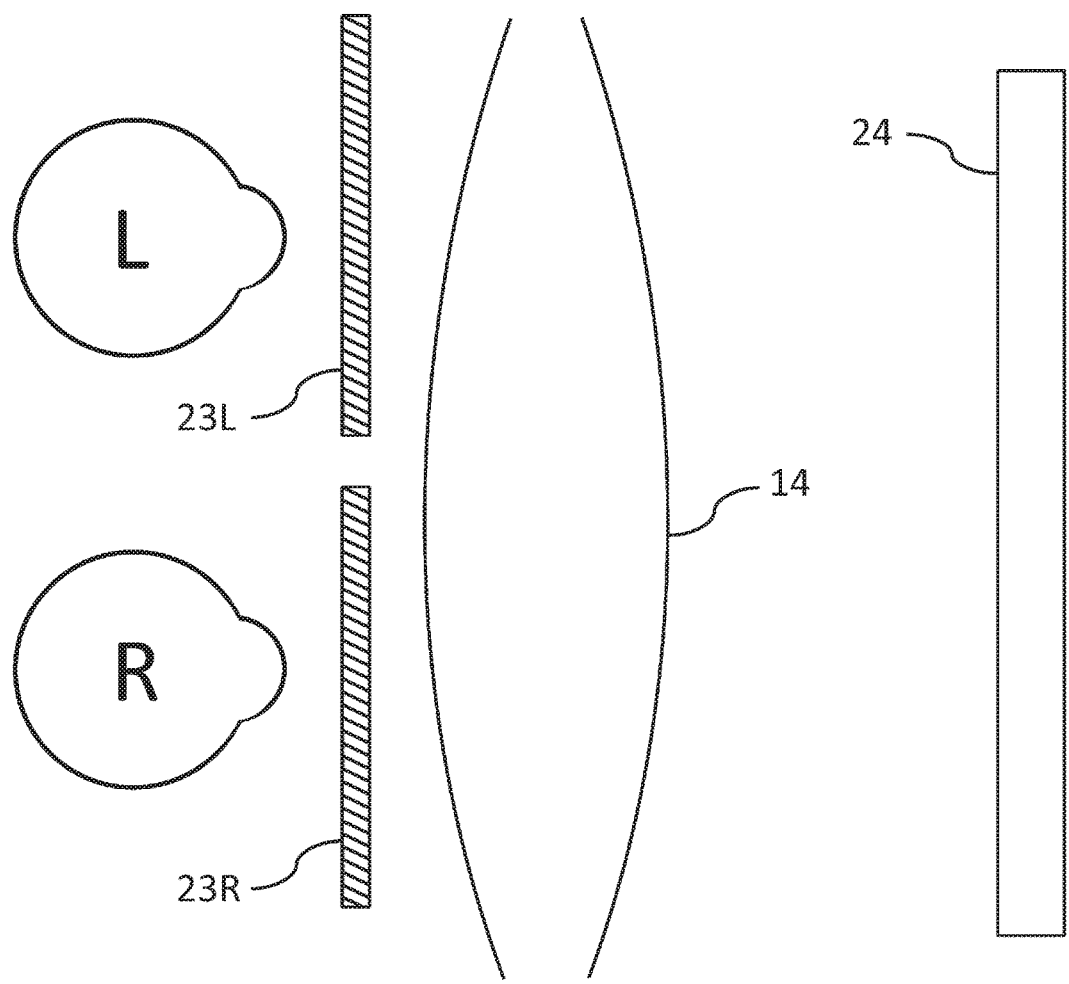
FIG. 9 is a front schematic view of a vision testing device using an active shutter and a time division display device, according to another embodiment of the present invention.

Explanation will be given next, using FIG. 9. FIG. 9 is a front schematic view of a vision testing device using an active shutter and a time division display device, according to another embodiment of the present invention.

As illustrated in FIG. 9, unlike the abovementioned embodiment, the light for suppressing the dark adaptation presented from the image display 13, is not continuously presented to the eye, but intermittently presented by an active shutter 23. In this case, open/close of the active shutter 23 is required to be performed at a cycle of not causing the dark adaptation to occur in the eye of the testee.

The target is presented as follows. First, the target is presented in the time division display device 24. The time division display device 24 always presents the background light. However, presentation of the target is performed in time division. In other words, presentation and non-presentation of the target is alternately repeated while presentation of the background light is continued. Then, on the assumption that the left eye L is tested, the active shutter 23L for the left eye is left open during presentation of the target to the left eye L. On the other hand, an active shutter 23R for the right eye not under the test, is operated. At this time, the timing of presenting and non-presenting the target and the timing of open/close of the active shutter 23R for the right eye, are synchronized in the time division display device 24. More specifically, the active shutter 23R for the right eye is set to be closed, so as not to present the target to the right eye R not under the test at the timing of performing presentation of the target in the dime division display device 24. Reversely, the active shutter 23R for the right eye is set to be opened to present the light for suppressing the dark adaptation to the right eye R at the timing of not performing presentation of the target in the time division display device 24.

In the modified example described here, the dark adaptation suppressing light presenting unit includes the time division display device 24. Further, the target presenting unit includes the active shutter 23 and the time division display device 24.

[Example of Using the Active Shutter (23 and 26) and the Screen]

Figure 10:
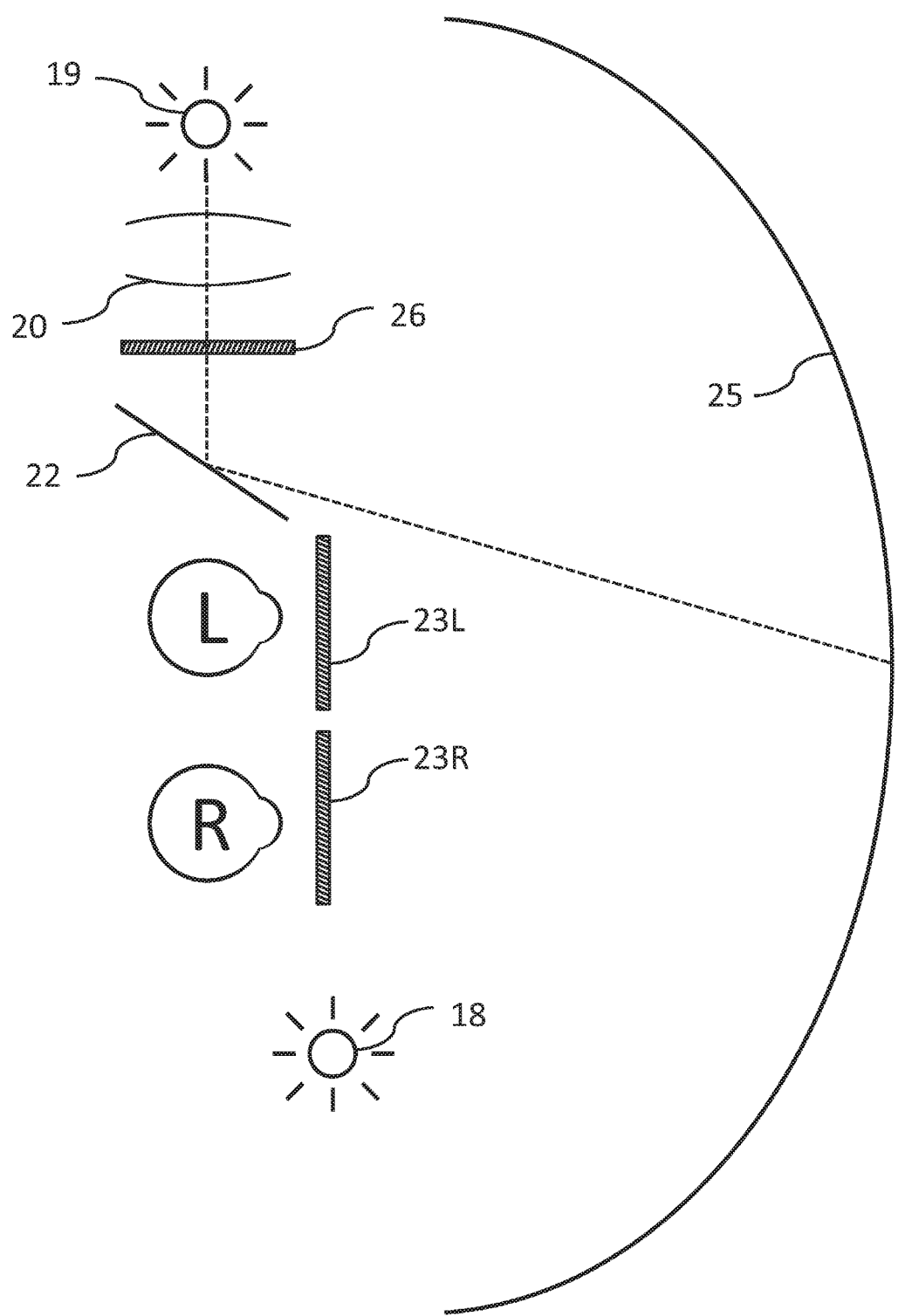
FIG. 10 is a front schematic view of a vision testing device using an active shutter and a screen, according to another embodiment of the present invention.

Explanation will be given finally, using FIG. 10. FIG. 10 is a front schematic view of a vision testing device using an active shutter (23, 26) and a screen 25, according to another embodiment of the present invention.

As illustrated in FIG. 10, the active shutter 23 may be applied to a screen system described in FIG. 8. The presented target passes through the optical system 20 from the light source 19 for the target, and the active shutter 26 for the target, and reflected by the reflector 22, and projected on the screen 25. When taking into consideration the case of testing the right eye R, the active shutter 23R for the right eye and the active shutter 26 for the target are synchronized in open/close of the shutter. In other words, when the active shutter 26 for the target is opened, the active shutter 23R for the right eye is also opened. On the other hand, open/close timing of the active shutter 23L for the left eye and open/close timing of the active shutter 26 for the target are deviated. That is, when the active shutter 26 for the target is opened, the active shutter 23L for the left eye is closed. Thus, the target can be presented to only the right eye R. In addition, the light for suppressing the dark adaptation is emitted in the interior of the test device, and therefore the dark adaptation can be suppressed for the left eye L not under the test.

In the modified example described here, the dark adaptation suppressing light presenting unit includes a non-polarized light source 18. Further, the target presenting unit includes the light source 19, the active shutter (23 and 26), and the screen 25 prepared separately from the dark adaptation suppressing light presenting unit.

A system of using the polarizer (15 and 21), a system of using the active shutter (23 and 26), and a combination of them may be applied to the abovementioned embodiment using the image display 13. Similarly, a system of using the polarizer (15 and 21), a system of using the active shutter (23 and 26), and a combination of them may be applied to a system using the screen (17 and 25).

Further, the abovementioned modified example shows that the effect of the present invention is exhibited even if not using HMD. However, in order to obtain a compact configuration of the vision testing device, HMD is preferably used.

Further, in the abovementioned embodiment, the case of using a perimeter as the vision testing device, has been mainly described. On the other hand, the present invention may be applied to the vision testing device other than the perimeter. For example, the present invention can be applied to a vision test device.

One of this embodiment will be described hereafter, with indicated by sings and numerals.

There is provided a vision testing device, including:

image displays (13L and 13R) configured to present a light for suppressing a dark adaptation for both eyes (L and R) of a testee; and image displays (13L and 13R) configured to present a target to an eye of the testee (L, R, or both) so that presentation of a target is performed to one of the eyes R before a vision testing for the other eye L is ended.

DESCRIPTION OF SIGNS AND NUMERALS

10 HMD unit
11 Housing
12 Wearing band
13 Image display
13α Polarizing film
14 Optical system
15 Polarizer
16 Polarizing beam splitter
17 Polarization holding screen
18 Light source (for a dark adaptation suppressing light)

19 Light source (for a target)
20 Optical system (for a target)
21 Polarizer (for a target)
22 Reflector
23 Active shutter
24 Time division display device
25 Screen
26 Active shutter (for a target)
30 Control computer
31 Communication unit
32 Data acquisition unit
33 Image generation unit
L Left eye
R Right eye

The invention claimed is:

1. A vision testing device, comprising:
   a dark adaptation suppressing light presenting unit configured to present, to both eyes of a testee, a background light for suppressing dark adaptation; and
   a target presenting unit configured to present, only under the presence of the background light, a target to at least one of the eyes of the testee, wherein the target is presented to one eye before a vision testing for the other eye is ended.

2. The vision testing device according to claim 1, wherein the dark adaptation suppressing light presenting unit is configured to present the background light to each of the both eyes with the same brightness.

3. The vision testing device according to claim 1, wherein the dark adaptation suppressing light presenting unit and the target presenting unit are assembled in a housing attachable to a head of the testee.

4. A computer readable non-transitory medium storing a vision testing program which causes a computer device of a vision testing device to control:
   a dark adaptation suppressing light presenting unit of the vision testing device to present, to both eyes of a testee, a background light for suppressing dark adaptation; and
   a target presenting unit of the vision testing device to present, only under the presence of the background light, a target to at least one of the eyes of the testee, wherein the target is presented to one eye before a vision testing for the other eye is ended.

5. The computer readable non-transitory medium according to claim 4, wherein the vision testing program causes the computer device to control the dark adaptation suppressing light presenting unit to present the background light to each of the both eyes with the same brightness.

6. The vision testing device according to claim 2, wherein the dark adaptation suppressing light presenting unit and the target presenting unit are assembled in a housing attachable to a head of the testee.

7. The vision testing device according to claim 1, wherein the target presenting unit is configured to present the target to one of the eyes at a time.

8. The computer readable non-transitory medium according to claim 4, wherein the vision testing program causes the computer device to control the target presenting unit to present the target to one of the eyes at a time.

9. The vision testing device according to claim 7, wherein the target presenting unit is configured to alternately present the target to each of the both eyes.

10. The computer readable non-transitory medium according to claim 8, wherein the vision testing program causes the computer device to control the target presenting unit to alternately present the target to each of the both eyes.

11. The vision testing device according to claim 1, wherein the background light is a white light.

12. The computer readable non-transitory medium according to claim 4, wherein the background light is a white light.

13. The vision testing device according to claim 1, wherein the background light has a brightness of not allowing the dark adaptation.

14. The computer readable non-transitory medium according to claim 4, wherein the background light has a brightness of not allowing the dark adaptation.

15. The vision testing device according to claim 1, wherein the target has a constant brightness.

16. The computer readable non-transitory medium according to claim 4, wherein the target has a constant brightness.

* * * * *